United States Patent
Shah et al.

[11] Patent Number: 5,993,834
[45] Date of Patent: Nov. 30, 1999

[54] METHOD FOR MANUFACTURE OF PIGMENT-CONTAINING COSMETIC COMPOSITIONS

[75] Inventors: Amit R. Shah, Commack; Carl C. Orr, Huntington; Nicole B. Huggins, Westbury, all of N.Y.

[73] Assignee: E-L Management Corp., New York, N.Y.

[21] Appl. No.: 08/957,827

[22] Filed: Oct. 27, 1997

[51] Int. Cl.$^6$ ................ A61K 6/00; A61K 7/00; A61K 7/04
[52] U.S. Cl. ............ 424/401; 424/61; 514/844; 514/845
[58] Field of Search ............ 424/401, 61; 514/844, 514/845

[56] References Cited

U.S. PATENT DOCUMENTS

| | | | |
|---|---|---|---|
| 3,546,008 | 12/1970 | Shields et al. | 117/138.8 |
| 3,734,874 | 5/1973 | Kibler et al. | 260/29.2 E |
| 3,779,993 | 12/1973 | Kibler et al. | 260/75 S |
| 4,233,196 | 11/1980 | Sublett | 260/29.2 N |
| 4,349,389 | 9/1982 | Schofield | 106/308 Q |
| 5,013,543 | 5/1991 | Mercado et al. | 424/63 |
| 5,055,500 | 10/1991 | Peters et al. | 523/319 |
| 5,143,671 | 9/1992 | Peters et al. | 264/117 |
| 5,169,881 | 12/1992 | Peters et al. | 523/319 |
| 5,260,052 | 11/1993 | Peters et al. | 424/63 |

FOREIGN PATENT DOCUMENTS

WO 96/03964  2/1996  WIPO.

OTHER PUBLICATIONS

HLB Emulsifier Selection System, Leon M. Price, in M. G. DeNavarre, "The Chemistry and Manufacture of Cosmetics", vol. III, Second Ed., (Continental Press, Orlando, 1975), pp. 25–37.

*Primary Examiner*—Thurman K. Page
*Assistant Examiner*—S. Howard
*Attorney, Agent, or Firm*—Dorene M. Price, Esq.; Karen A. Lowney, Esq.

[57] ABSTRACT

The present invention relates to a pigment composition comprising a pigment treated with a water-dispersible polyester or polyesteramide polymer in the absence of added water. The invention also relates to a method grinding a mixture containing of a pigment with a water-dispersible polyester or polyesteramide in the absence of added water. Such pigment compositions are particularly useful as the colorant in cosmetic compositions.

25 Claims, No Drawings

METHOD FOR MANUFACTURE OF PIGMENT-CONTAINING COSMETIC COMPOSITIONS

FIELD OF THE INVENTION

The present invention relates to a method for making cosmetic compositions. In particular, the invention relates to a method for making pigment-containing cosmetics by coating pigments with a water dispersible polymer.

BACKGROUND OF THE INVENTION

The manufacture of color cosmetics, such as foundations, blushes, eyeshadows, lipsticks, as well as other colored materials, such as inks, necessarily involves a step of incorporating pigments into the formulation. When the final product has a liquid, particularly aqueous, base, the incorporation of the pigment is problematic, as the most commonly used pigments, such as titanium or iron oxides, are insoluble particles which do not easily blend into the liquid base. These particles can be physically dispersed in water. Once incorporated, however, particles can tend to reagglomerate due to the natural incompatibility of the pigments with water in the formulation; particles can also be adversely affected by the liquid environment, resulting in a loss of color stability. This can give rise to a product which is non-uniform, and unacceptable both to the manufacturer and to the average consumer.

In an effort to enhance the dispersibility of pigment particles and to hinder tendencies for reagglomeration, the industry has often turned to coating of pigment particles. Pigment coatings are chosen for their ability to render the coated particles more compatible with the environment in which they are to be used. Such coating materials are well-known, and have been described for example in U.S. Pat. Nos. 4,349,389; 5,013,543; 3,546,008; 3,734,874; 3,779,993; and 4,233,196. The coatings described in the latter four references, which are polyesters and polyesteramides, are particularly useful for preparing water-dispersible pigments. However, the recommended method for preparation and dispersion of the coated pigments is a wet process, using relatively small quantities of coating. Although to some extent effective, this methodology can result in incomplete coating of the pigment, which can ultimately permit reaggregation of the pigments. The wet preparation process also results, even after drying, in a pigment which does not store well for long periods of time and may be subject to bacterial contamination. The present invention now provides a dry treated pigment which is stable even after prolonged storage time, and which disperses easily, and without reagglomeration, in an aqueous base.

SUMMARY OF THE INVENTION

The present invention provides a pigment composition comprising pigment particles treated with a water-dispersible polyester or polyesteramide in the absence of water. The invention also comprises a method for manufacturing the pigment composition comprising co-grinding pigment and the water-dispersible polymers in the substantial absence of water. Also provided are cosmetic compositions comprising the pigment composition.

DETAILED DESCRIPTION OF THE INVENTION

The method for preparing the pigment compositions of the present invention utilizes readily available starting materials. The preferred water-dispersible coatings are polyesters and polyesteramides, such as are available from Eastman Chemical Corporation, under the tradename Eastman AQ Polymers. These polymers are described, for example, in U.S. Pat. Nos. 3,546,008; 3,734,874; 3,779,993; and 4,233,196, the contents of which are incorporated herein by reference. Pigment particles precoated with these polymers are commercially available from Eastman, and have been described, for example, in U.S. Pat. Nos. 5,260,052; 5,143,671, and 5,055,500, also incorporated herein by reference; their use in cosmetic compositions has also previously been described, for example, in U.S. Pat. No. 5,169,881 and WO 96/03964. However, in each case, the coated pigment compositions are prepared by a "wet" process: the pigment and coating polymer are combined together in the presence of a significant quantity, i.e., from 5 up to 50%, of water in the total starting mixture. Although the pigment composition so formed can be subsequently dried, it is virtually inevitable that some water will remain in the formulation.

In contrast, the pigment composition of the present invention is prepared by an essentially dry process, i.e., the components are simply dry-ground together on a standard roller mill, in the absence of any added water, to the appropriate particle size. The resulting pigment composition needs no further drying, and can be stored for long periods of time with little threat of bacterial contamination promoted by the presence of residual water in the formulation.

As noted above, the polyesters and polyesteramides useful in the invention are known compounds and commercially available. The polymers of the present invention are such linear water-dispersible polyesters or polyesteramides which are reaction products of the following reactants, or the ester- or esteramide-forming derivatives thereof:

(1) at least one difunctional dicarboxylic acid;

(2) from 2–25 mole % of at least one difunctional sulfomonomer containing at least one metallic sulfonate group or nitrogen-containing non-metallic sulfonate group attached to an aromatic or cycloaliphatic nucleus wherein the functional groups are hydroxy, carboxyl or amino, or a mixture thereof;

(3) at least one difunctional reactant selected from a glycol, or a mixture of a glycol having two -NRH groups, the glycol containing two —$CH_2$—OH groups; and (4) from 0–40 mole % of a difunctional reactant selected from hydroxycarboxylic acids having one —$C(R)_2$—OH group, aminocarboxylic acids having one —NRH group, and amino alcohols having one —$C(R)_2$—OH group and one —NRH group, of mixtures thereof;

wherein each R of (3) and (4) is H or an alkyl group containing 1 to 4 carbon atoms, and all mole percentages are based on the total of all acid, hydroxyl, and amino equivalents being equal to 200 mole %.

The polymers employed in the pigment composition have an inherent viscosity of at least 0.1, and preferably at least 0.3, and a glass transition temperature of from 25° C. to 90° C. when the polymer is in the dry state. Preferred polymers are those having an dicarboxylic acid component, a difunctional sulfomonomer component, and a glycol component, especially those having an aromatic dicarboxylic acid moiety, an aliphatic or cycloaliphatic glycol residue, and on average, per molecule, between five and eight sodiosulfo ($SO_3^-Na^+$) substituents on the aromatic dicarboxylic acid units. Particularly preferred is the polymer known as AQ 55S, available from Eastman Chemical Company.

The pigment component of the present composition can be any which is insoluble or sparingly soluble in water. The pigment compositions have utility in virtually any industry in which water dispersible pigments are used, for example, in manufacturing inks or other industrial pigmented product, and the pigment utilized will be chosen accordingly. However, a preferred use of the compositions is for cosmetic applications, and in this case, the pigment is chosen from those which are cosmetically acceptable. In general, the pigments employed may be organic or inorganic. However, it will be apparent that the choice of pigment should preferably not include those having large amounts of bivalent or multivalent ionizable cations which can interfere with the water dispersibility of the polyester component. Choice of pigment should also be made keeping in mind the temperature at which the grinding process will take place, so as to avoid pigments which are not stable at the processing temperature.

Examples of useful inorganic pigments include iron oxides (yellow, red, brown or black), ferric ammonium ferrocyanide(blue), manganese violet, ultramarine blue, chrome oxide(green), talc, lecithin modified talc, zeolite, kaolin, lecithin modified kaolin, titanium dioxide(white) and mixtures thereof. Other useful pigments are pearlants such as mica, bismuth oxychloride and treated micas, such as titanated micas and lecithin modified micas.

The organic pigments include natural colorants and synthetic monomeric and polymeric colorants. Exemplary are phthalocyanine blue and green pigment, diarylide yellow and orange pigments, and azo-type red and yellow pigments such as toluidine red, litho red, naphthol red and brown pigments. Also useful are lakes, which are pigments formed by the precipitation and absorption of organic dyes on an insoluble base, such as alumina, barium, or calcium hydrates. Particularly preferred lakes are primary FD&C or D&C lakes and blends thereof.

Also included are copolymer pigments that are water insoluble, e.g., nylon powder, polyethylene, and polyesters. The polyesters can include linear, thermoplastic, crystalline or amorphous materials produced using one or more diols and one or more dicarboxylic acids copolymerized with colorants. Other pigments to be used in the invention will be apparent to one of ordinary skill in the art.

Although the polyester will be plasticized to some extent by the heating which takes place during the grinding process, it is preferred that a separate plasticizer also be employed. The plasticizer may be any which are capable of softening the polyester component being used. Preferred plasticizers are glycols, such as 1,3-butylene glycol or propylene glycol, but other examples include, but are not limited to, dibutyl phthalate, camphor, polysorbates, such as Tween 20, and citrates, such as butyloctyl citrate.

The pigment composition does not require the presence of a surfactant; however, the use of one may facilitate the combination of the pigment and polymer. Any type of surfactant, for example, nonionic, amphoteric, anionic or cationic, can be employed. However, when a surfactant is used, it is preferably a nonionic surfactant. A particularly preferred surfactant for the present composition is Laureth-7.

To initiate the preparation of the pigment composition, the polymer is simply mixed with the pigment, the plasticizer, and if used, the surfactant. For purposes of dry grinding each of the polymer and pigment component can be present in an amount ranging from about 20 to about 80%. In a preferred embodiment, however, the pigment is present in an amount of at least about 50%, more preferably at least about 60%, and most preferably at least about 70%, while the polymer is present in an amount of about 20–50%, more preferably about 20–30%, each by weight of the total composition. When used, the plasticizer is present in an amount of from about 1–10% and the surfactant in an amount of from about 0.5–2%. The grinding procedure is one which is standard in the art. In brief, the method involves combining the pigment, polymer, and other optional ingredients, in the absence of any added water. The mixture of components is passed, several times, through a standard two roller mill, with one cold roller, and the second roller heated to about the glass transition temperature of the polymer, to grind the materials down to an average particle size no greater than $0.5-15\mu$. The mixture is then removed from the roller mill in the form of chips or sheets, which are then pulverized to a form dispersible in an aqueous base.

The pigment compositions and this method of preparation have a number of advantages. First, the dry grinding is generally more efficient than wet processing for bringing down the particle size to $5\mu$ or less, which is the preferred size for cosmetic compositions. Also, the resulting dry product contains substantially no water, generally less than 1%, and therefore does not provide a hospitable environment for bacterial growth; the dried compositions remain stable for prolonged period with no contamination. The dried chips remain separate, with substantially no reaggregation, indefinitely during storage; moreover, there is little or no reagglomeration of the particles when dispersed in an aqueous medium, whereas the wet processed coated pigments have a greater tendency to reagglomerate.

A particularly unexpected advantage is that there is little or no color transfer from pigments which are prepared in this way. The wet-coated pigments tend to permit a bleed of water-dispersible dye when dispersed in an aqueous base, which bleeding can lead to color transfer. In contrast, the dry-milled pigments do not exhibit any bleeding when so dispersed. This property makes them particularly well suited for use in aqueous based color cosmetics, such as mascara, eyeliner, blush, foundation, eyeshadows and the like. Cosmetics prepared with the composition of the invention show substantial transfer resistance.

The pigment composition can be readily incorporated as a component of a suspension, dispersion or emulsion. The emulsion may be an oil-in-water emulsion, or a water-in-oil emulsion. These emulsions contain one or more oil components, an aqueous component, and a specific emulsifier component chosen depending on the nature of the desired emulsion.

Methods and components of cosmetic emulsions are well known in the art. Briefly, the oil component may be any pharmaceutically or cosmetically acceptable material which is substantially insoluble in water. These materials can be found for example in the CTFA International Dictionary of Cosmetic Ingredients as well as the U.S. Pharmacopoeia or equivalent sources. Suitable oil components include, but are not limited to, natural oils, such as coconut oil; hydrocarbons, such as mineral oil and hydrogenated polyisobutene; fatty alcohols, such as octyldodecanol; esters, such as C12–15 alkyl benzoate; diesters, such as propylene glycol dipelargonate; triesters, such as glyceryl trioctanoate; sterol derivatives, such as lanolin; animal waxes, such as beeswax; plant waxes, such as carnauba; mineral waxes, such as ozokerite; petroleum waxes, such as paraffin wax; synthetic waxes, such as polyethylene; and mixtures thereof. Suitable oil components may also be silicones including, but not limited to, volatile silicones such as cyclomethicone; polymeric silicones such as dimethicone; alkylated derivatives of polymeric silicones, such as cetyl dimethicone and lauryl trimethicone; hydroxylated derivatives of polymeric silicones, such as dimethiconol; and mixtures thereof. The aqueous component refers to any pharmaceutically or cosmetically acceptable material consisting essentially or predominantly of water.

For preparation of an oil-in water emulsion, the oil-in-water emulsifier will be an emulsifier having a hydrophilic-lipophilic balance (HLB) of at least 6, or a mixture of such emulsifiers with one or more water-in-oil emulsifiers(i.e., emulsifiers having an HLB of from about 2 to about 6), in which case the type and amount of each emulsifier present in the mixture is selected such that the effective HLB of the resultant oil-in-water emulsifier component is at least about 6. Techniques for combining and ascertaining the effective HLB of a mixture of emulsifiers are known; see L. M. Prince, in M. G. DeNavarre, "The Chemistry and Manufacture of Cosmetics", Volume III, Second Ed., (Continental Press, Orlando, 1975), pp. 25–37.

Suitable oil-in-water emulsifiers include, but are not limited to, sorbitol derivatives, such as sorbitan monolaurate and polysorbate 20; ethoxylated alcohols such as laureth-23; ethoxylated fatty acids such as PEG-1000 stearate; amidoamine derivatives such as stearamidoethyl diethylamine; sulfate esters such as sodium lauryl sulfate; phosphate esters such as DEA cetyl phosphate; fatty acid amine salts such as TEA stearate; and mixtures thereof.

The emulsion may also be a water-in-oil emulsion. For this purpose, a water-in-oil emulsifier is employed. This refers to any cosmetically acceptable emulsifier having an HLB of no greater than 6, preferably from about 2 to about 4. Suitable water-in-oil emulsifiers include, but are not limited to, sorbitan derivatives such as sorbitan laurate and sorbitan palmitate; alkoxylated alcohols such as laureth-4; hydroxylated derivatives of polymeric silicones, such as dimethicone copolyol; alkylated derivatives of hydroxylated polymeric silicones, such as cetyl dimethicone copolyol; glyceryl esters such as polyglyceryl-4 isostearate; beeswax derivatives such as sodium isostearoyl-2 lactylate; lecithin; and mixtures thereof.

To incorporate the pigment composition into a formulation, water is heated to 70° C. under agitation; the treated pigment chips are added to the water, mixed in and allowed to dissolve. Alternately, the chips can be added directly to a preformed emulsion. The invention is further illustrated by the following non-limiting examples.

EXAMPLES

Example 1

A pigment composition containing the following components is prepared:

| Material | Weight % |
|---|---|
| Cosmetic Black | 72.40 |
| Eastman AQ 55S Polymer | 24.00 |
| Laureth-7 | 1.00 |
| 1,3 Butylene Glycol | 2.50 |

The pigment is placed in a Sigma blender, and the polymer added to it, at room temperature. The laureth-7 and butylene glycol are then added, and all components are mixed until homogeneous. The mixture is removed from the blender, and rolled on a Ross roller mill, with the front roller cold and the rear roller heated with steam to 56° C.

Example 2

The dry coated pigment composition of the invention is added to a makeup formulation, and compared with identical formulations containing coated pigments prepared in a different manner. Specifically, three identical oil in water emulsions are prepared containing (1) the dry-processed polymer coated pigments of the invention; (2) wet-processed pigment coated with the same polymer; and (3) uncoated pigment and separately-added polymer. The formulations are observed over a period of at least three months. Formula 1, with the claimed pigment compositions, remained stable, with no shade shifting after a period of over three months. In contrast, formula 2 shows shade shifting virtually immediately, during processing, probably as a result of pigment bleeding and/or reagglomeration of particles. Formula 3 showed gelling and tackiness after a period of two months. These comparative data show the superiority of the pigment composition prepared by dry-grinding polymer and pigment together.

What we claim is:

1. A pigment composition comprising a pigment treated with a water-dispersible polyester or polyesteramide polymer, and a plasticizer in the absence of added water.

2. The composition of claim 1 in which the polymer has a dicarboxylic acid component, a sulfomonomer component, and a glycol component.

3. The composition of claim 1 which comprises at least about 50% pigment.

4. The composition of claim 1 which comprises at least about 70% pigment.

5. The composition of claim 1 in which the pigment is an inorganic pigment.

6. The composition of claim 1 in which the pigment is iron oxide.

7. The composition of claim 1 in which the treated pigment has an average particle size of from about 0.5–15$\mu$.

8. The composition of claim 1 which also comprises a surfactant.

9. A pigment composition which comprises pigment in an amount of about 20–80%, treated with a water-dispersible polyester or polyesteramide polymer having a dicarboxylic acid component, a sulfomonomer component, and a glycol component, in an amount of about 1–10%, in the absence of added water.

10. The composition of claim 9 in which the polymer comprises a dicarboxylic acid component, a difunctional sulfomonomer component, and a glycol component.

11. The composition of claim 9 in which the polymer comprises an aromatic dicarboxylic acid moiety, an aliphatic or cycloaliphatic glycol residue, and an average, per molecule, of between five and eight sodiosulfo($SO_3^-Na^+$) substituents on the aromatic dicarboxylic acid units.

12. The composition of claim 9 in which the pigment is present in an amount of from about 70–80%, and the polymer is present in an amount of about 20–30%.

13. The composition of claim 10, which comprises a surfactant in an amount of from about 0.5–2%.

14. A pigment composition which comprises an inorganic pigment in an amount of about 70–80%, treated with a water-dispersible polyester or polyesteramide polymer having an aromatic dicarboxylic acid moiety, an aliphatic or cycloaliphatic glycol residue, and an average, per molecule, of between five and eight sodiosulfo($SO_3^-Na^+$) substituents on the aromatic dicarboxylic acid units, in an amount of about 20–30%, and a butylene or propylene glycol plasticizer in an amount of from about 1–10%, in the absence of water.

15. The composition of claim 14 in which the pigment is an iron oxide.

16. The composition of claim 15 which also comprises a nonionic surfactant in an amount of from about 0.5–2%.

17. A method of making a pigment composition comprising grinding a mixture containing a pigment with a water-dispersible polyester or polyesteramide, and a plasticizer in the absence of added water.

18. The method of claim 17 in which the composition is ground on a roller mill.

19. The method of claim 17 in which the pigment composition is prepared by
  (a) mixing together the pigment with the water dispersible polyester or polyesteramide, and with a plasticizer and surfactant if used; and
  (b) grinding the mixture obtained in step (a) on a two-roller mill, for a time sufficient to obtain a particle size of 0.5–0.15μ.

20. The method of claim 19 in which one roller of the roller mill is cold, and the other roller is heated to the glass transition temperature of the polymer.

21. A composition prepared by the method of claim 17.

22. A cosmetic composition comprising a colorant-effective amount of the pigment composition of claim 1.

23. A cosmetic composition comprising a colorant-effective amount of the pigment composition of claim 9.

24. A cosmetic composition comprising a colorant-effective amount of the pigment composition of claim 14.

25. A cosmetic composition comprising a colorant-effective amount of the pigment composition of claim 17.

* * * * *